United States Patent
Hicken et al.

(10) Patent No.: US 6,540,752 B1
(45) Date of Patent: Apr. 1, 2003

(54) THREADED BONE TUNNEL DILATOR

(75) Inventors: Greg Hicken, 1285 Cedar Heights, Logan, UT (US) 84341; Greta Jo Hays, Logan, UT (US); T. Wade Fallin, Hyde Park, UT (US)

(73) Assignee: Greg Hicken, Logan, UT (US)

( * ) Notice: Subject to any disclaimer, the term of this patent is extended or adjusted under 35 U.S.C. 154(b) by 0 days.

(21) Appl. No.: 09/432,477

(22) Filed: Nov. 1, 1999

(51) Int. Cl.⁷ .............................................. A61B 17/60
(52) U.S. Cl. ....................................................... 606/90
(58) Field of Search .............................. 606/53, 79, 80, 606/90, 105, 180, 81

(56) References Cited

U.S. PATENT DOCUMENTS

| | | | | |
|---|---|---|---|---|
| 5,259,398 A | * | 11/1993 | Vrespa | 128/898 |
| 5,342,363 A | * | 8/1994 | Richelsoph | 606/79 |
| 5,350,380 A | * | 9/1994 | Goble et al. | 606/80 |
| 5,443,468 A | | 8/1995 | Johnson | |
| 5,496,326 A | | 3/1996 | Johnson | |
| 5,573,537 A | * | 11/1996 | Rogozinski | 606/80 |
| 5,628,752 A | * | 5/1997 | Asnis et al. | 606/104 |
| 5,690,634 A | * | 11/1997 | Muller et al. | 606/80 |
| 5,908,423 A | * | 6/1999 | Kashuba et al. | 606/80 |
| 5,931,841 A | * | 8/1999 | Ralph | 606/85 |
| 5,941,706 A | * | 8/1999 | Ura | 433/165 |
| 6,071,284 A | * | 6/2000 | Fox | 606/80 |

OTHER PUBLICATIONS

Arthrex, "TransFix ACL Reconstruction", Section 2.0.: Joint Preparation and Tunnel Positioning, p. 3 (undated).
Instrument Makar, Inc., "First in Compaction", one (1) page (undated); and.
SulzerMedica, "6 Tibial Tunnel", four (4) pages, (undated);.
Arthrex, ACL Tunnel Preparation Instrumentation Set, two (2) pages.

\* cited by examiner

Primary Examiner—Eduardo C. Robert
(74) Attorney, Agent, or Firm—Pandiscio & Pandiscio, P.C.

(57) ABSTRACT

A cannulated threaded bone tunnel dilator that accurately advances through bone and dilates a bone tunnel in a gentle, controlled manner, including a distal tapered, threaded tip and a body mounted on the distal end of a shaft. The proximal end of the shaft includes a drive attachment for rotating the dilator so as to threadingly advance the dilator. In use, a guidewire is driven into bone, and then the surgeon advances the dilator along the guidewire until the tip of the dilator engages the bone. The surgeon then rotates the dilator clockwise so as to threadingly advance the dilator through the bone until the dilator reaches a desired depth. After reaching the desired depth, the surgeon removes the dilator by rotating the dilator counterclockwise and retracting the dilator from the then-compacted bone tunnel. The peaks and troughs of the dilator's thread compact the bone so as to create the dilated bone tunnel. However, the peaks and troughs do not extend beyond a smooth cylindrical body, thus, following dilation, the resultant bone tunnel is smooth and compacted.

38 Claims, 4 Drawing Sheets

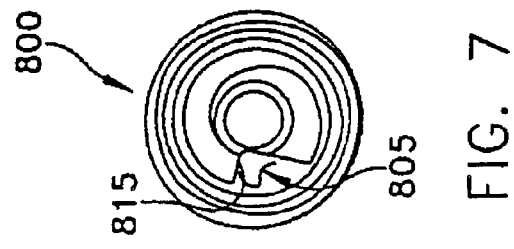
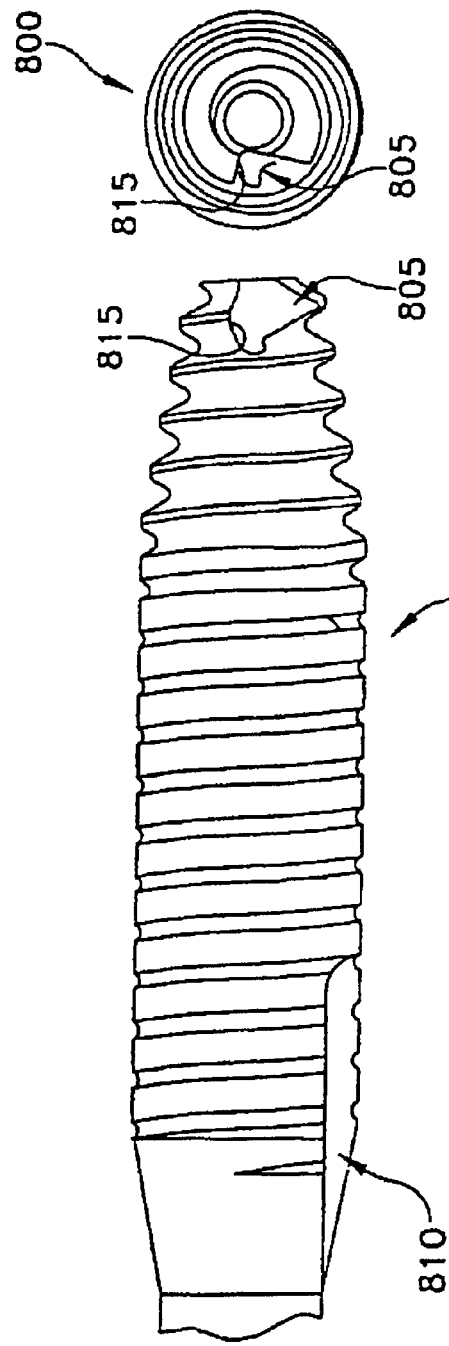
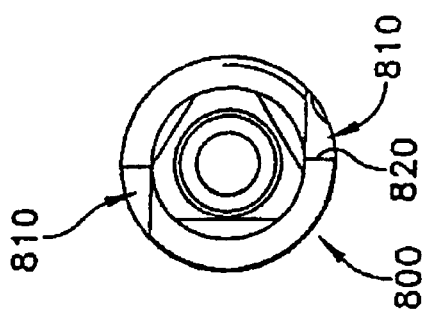
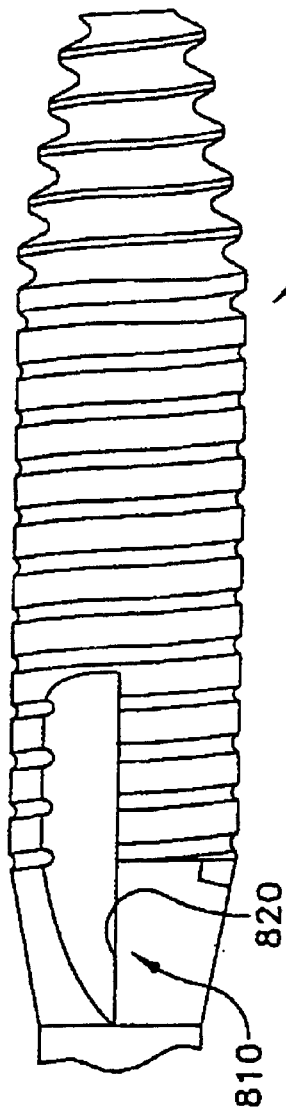

ardThREADED BONE TUNNEL DILATOR

FIELD OF THE INVENTION

This invention relates to attaching tissue and non-tissue members to bone. More specifically, this invention relates to dilating a bone tunnel so as to improve member attachment to a bone.

BACKGROUND OF THE INVENTION

Many medical procedures involve attaching tissue or an artificial member to, or inside of, a bone. For example, repairing a detached ligament frequently involves re-attaching the detached ligament to the bone. Often, the repair involves removing the damaged tissue and replacing it with a graft or artificial substitute.

Many techniques exist for attaching a natural or artificial member to a bone. Sometimes the member is drawn to, and/or secured in, a bone tunnel in the bone. For example, referring to FIG. 1, to repair a damaged knee ligament, such as an anterior cruciate ligament (ACL) or a posterior cruciate ligament (PCL), the damaged ligament is often replaced with a graft ligament. Replacing the damaged ligament with a graft ligament involves attaching the graft ligament to the patient's femur and tibia. This is typically done by forming a bone tunnel $B_1$ in the tibia T, and a coincidental bone tunnel $B_2$ in the femur F. A graft ligament L is then threaded into the bone tunnels $B_1$ and $B_2$. One end of the graft ligament L is attached to the tibia T, and the other end of the graft ligament L is attached to the femur F.

In some cases, the distal end of the graft ligament L is secured to the femur F with an interference screw (not shown) which wedges the graft ligament laterally against the side wall of the bone tunnel $B_2$. The interference screw simultaneously engages both the side wall of the bone tunnel and a portion of the graft ligament L, thereby fixing the graft ligament to the bone with an interference coupling. It will be appreciated that with such an arrangement, secure attachment of the graft ligament L in the bone tunnel depends on the quality and integrity of the side wall of the bone tunnel, as well as the effectiveness of the attachment mechanism which is used to attach the graft ligament to the bone.

Sometimes a member. (both tissue and non-tissue) is mounted on, rather than in, a bone. Although the member may be mounted on the bone, the attachment mechanisms for securing the member to the bone are frequently secured in a bone tunnel. For example, and referring now to FIG. 2, to mount a ligament L on a bone N, the surgeon may create a bone tunnel $B_3$ in the bone N and then insert a suture anchor A in the bone tunnel so that the suture anchor's sutures S extend out of the bone tunnel. Thereafter, the sutures S may be used to secure the ligament L to the bone in ways well known in the art, e.g., by tying a knot K atop a washer W. Again, secure attachment of the anchor A in the bone tunnel depends on the quality and integrity of the side wall of the bone tunnel, as well as the effectiveness of the attachment mechanism of the anchor.

Typically, the surface and integrity of a bone is not highly predictable. For example, a bone does not have constant consistency and hardness throughout. Typically, a bone has a hard cortical outer shell and a soft cancellous inner core. The shell is relatively thin as compared with the core, especially in large bones such as the tibia and femur. This is significant because, when a member (both tissue and non-tissue) is attached to a bone by means of a bone tunnel, a significant portion of the attachment typically occurs in the soft cancellous bone. Thus, the quality of the attachment is typically heavily dependent on the quality of the cancellous bone defining the side walls of the bone tunnel. The quality of the cancellous core varies significantly from person to person and bone to bone.

To achieve a high-quality attachment, the cancellous bone tunnel must provide a high-quality surface and integrity. If the side wall of the bone tunnel provides a poor-quality surface, for example with too many fractures and/or striations, the member may not be well secured to the bone. Similarly, if the side wall of the bone tunnel provides poor integrity, e.g., an integrity like unpacked snow, the member also may not be well secured to the bone.

Furthermore, where a ligament is being mounted directly in one or more bone tunnels (e.g., such as in the ligament reconstruction depicted in FIG. 1), it is generally important that the ligament osseo-integrate with the side wall(s) of the bone tunnel(s). If the side wall of a bone tunnel provides a poor-quality surface or poor integrity, such osseo-integration will be impeded.

To enhance high-quality attachment in a bone tunnel, surgeons have developed a procedure to enhance the quality and integrity of the side wall of the bone tunnel. This is done by dilating the bone tunnel so as to enhance the density of the bone forming the side wall of the bone tunnel. More particularly, such dilation involves packing the soft cancellous bone outward, in a fashion similar to compacting soft snow. Such prior art dilation typically involves drilling a hole of a pre-determined size into the bone. The drill is typically then removed and a dilator, slightly larger than the aforementioned pre-determined size, is forced through the hole, commonly by hammering. As the dilator advances through the hole, the dilator pushes interfering cancellous bone radially outward. The dilator also pushes the interfering cancellous bone distally.

Because the prior art dilation process typically involves intermittent, sudden forward surges of the dilator, the process is traumatic and may result in inconsistent compacting of the bone. This inconsistent compacting of the bone can also cause the quality and integrity of the side wall of the bone tunnel to vary. Surge advancement also increases the potential for the dilator to assume a path which may be aligned with the direction of the dilator-driving force, rather than the path defined by the original bone hole. In this respect it should be appreciated that an incorrectly-located bone tunnel may cause significant mis-alignment of a ligament attached therein. This can be especially true in the case of an ACL or PCL reconstruction, where such mis-alignment can have serious, long-term, debilitating consequences for the patient.

Thus, what is needed is a novel dilator that accurately advances through a bone and dilates a bone tunnel in a gentle, controlled manner.

SUMMARY OF THE INVENTION

The present invention is a threaded bone tunnel dilator that accurately advances through a bone and dilates a bone tunnel in a gentle, controlled manner. The invention is applicable to any attachment in a bone tunnel or bone canal. The invention provides for progressively expanding a bone tunnel or canal laterally, without significant expansion longitudinally. The invention also provides for dilating a bone tunnel in a gentle, yet extensive manner, without substantial drilling or cutting. The invention also provides for defining a compacted bone tunnel with a smooth or textured surface. The invention provides improved elements and arrangements thereof, in an apparatus and method for the purposes described, which are inexpensive, dependable, and effective in accomplishing its intended purposes.

An embodiment configured according to the principles of the present invention includes a distal, tapered threaded tip and a body mounted on the distal end of a shaft. The proximal end of the shaft includes a drive attachment for rotating the dilator so as to threadingly advance the dilator through bone. The dilator is preferably cannulated so that it can be advanced along a guidewire.

In one preferred method of use, the surgeon first drives a guidewire into the bone. Once the guidewire is emplaced, the surgeon places the dilator over the guidewire, advances the dilator along the guidewire, and engages the bone. Rotating the dilator clockwise threadingly advances the dilator through the bone, until the dilator reaches a desired depth. The tapered leading threads of the dilator open the bone through dilation so as to define the bone tunnel. The trailing smooth cylindrical body smoothes and further compacts the side wall of the bone tunnel. After reaching the desired depth, the surgeon removes the dilator by rotating the dilator counterclockwise so as to threadingly retract the dilator from the then-compacted bone tunnel.

These and other features of the present invention will be more readily appreciated in view of the attached drawings and the detailed description provided below.

BRIEF DESCRIPTION OF THE DRAWINGS

The invention is described in detail below with reference to the following drawings, throughout which similar reference characters denote corresponding features, and wherein:

FIG. 6 is a side elevational view of an additional form of dilator formed in accordance with the present invention;

FIG. 7 is a front view of the embodiment of FIG. 6;

FIG. 8 is a rear view of the embodiment of FIG. 6; and

FIG. 9 is a view like that of FIG. 6, except that the dilator has been rotated 90° in a counterclockwise direction.

DETAILED DESCRIPTION OF THE INVENTION

The present invention is a threaded bone tunnel dilator that accurately advances through a bone and dilates a bone tunnel in a gentle, controlled manner.

Figure 1:
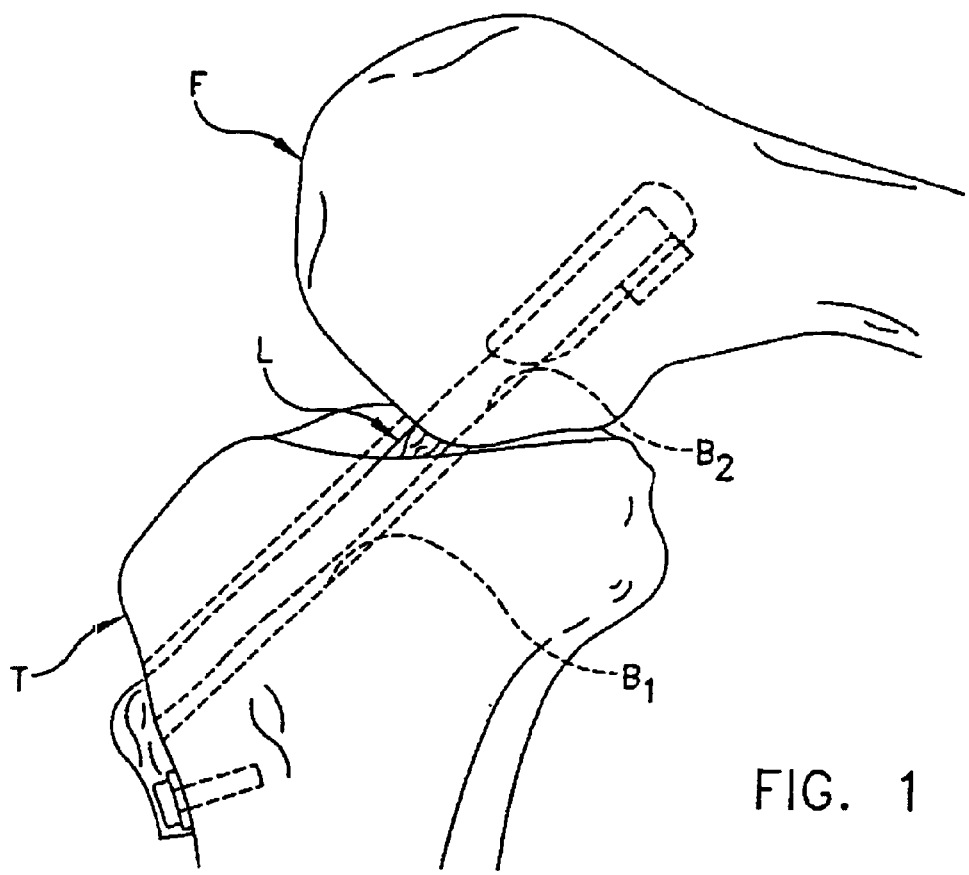
FIG. 1 a schematic side view showing a graft ligament attached to a femur and tibia.
Figure 2:
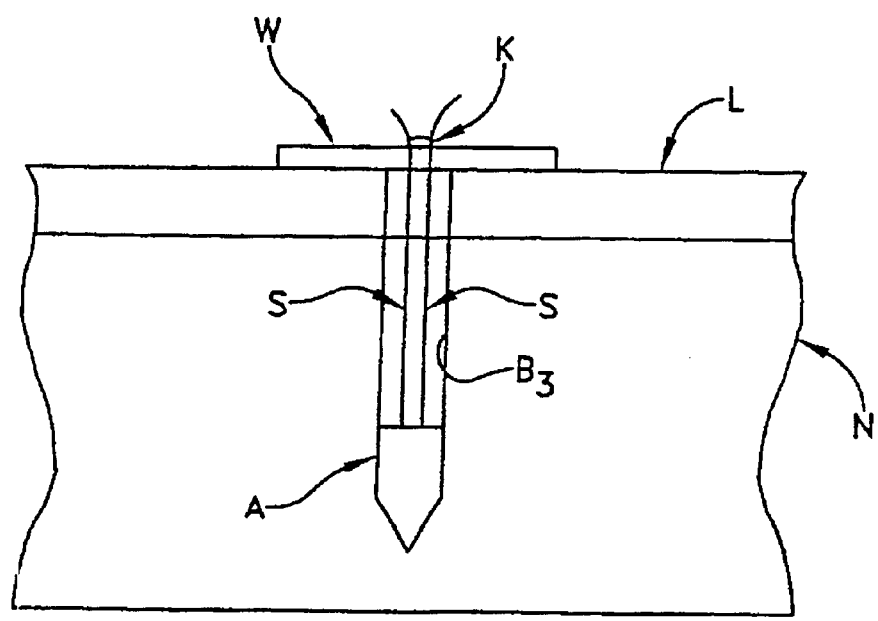
FIG. 2 is a schematic side view showing a suture anchor securing a ligament to a bone.
Figure 3:
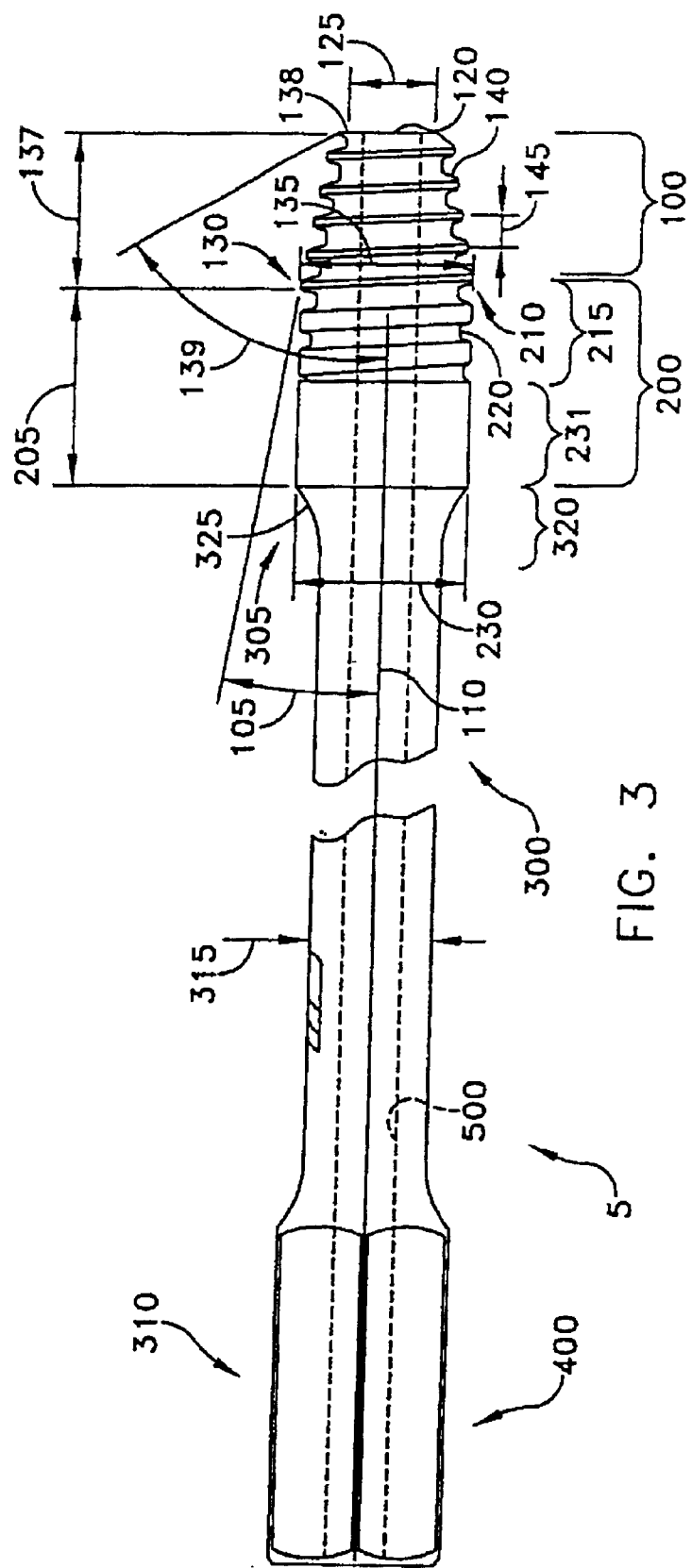
FIG. 3 is a side elevational view of a threaded dilator formed in accordance with the present invention.

Referring now to FIG. 3, there is shown a dilator 5 which comprises a preferred form of the invention. Dilator 5 generally comprises a distal threaded tip 100 and a body 200 mounted on the distal end of a shaft 300. The proximal end of the shaft 300 includes a drive attachment 400 for rotating the dilator so as to threadingly advance the dilator.

The tip 100 is configured so as to have a taper 105. The taper 105 causes the dilator to open the bone and to be self-centering during bone tunnel dilation. This self-centering feature is especially helpful when the invention is not used in conjunction with a guidewire. To this end, the taper 105 is preferably about 5 to about 30 degrees with respect to the longitudinal axis 110. In one preferred embodiment of the invention, the taper 105 is preferably about 10.85 degrees with respect to the longitudinal axis 110. To achieve this taper of about 10.85 degrees, in one preferred embodiment of the invention, the distal end 120 of tip 100 has a diameter 125 of about 0.128 inches, the proximal end 130 of tip 100 has a diameter 135 of about 0.354 inches, and the length 137 between the two diameters 125 and 135 of about 0.381 inches. However, it should also be appreciated that the taper 105 may be adjusted to any angle which may be more appropriate for a particular application.

The taper 105 may also assume any profile which promotes optimal bone compaction. For example, the taper 105 may be a straight taper as shown. The taper 105 also may be a compound taper, consisting of different straight tapers defining unique angles with respect to the longitudinal axis 110 of tip 100. Alternatively, the taper 105 may also assume a parabolic or elliptical shape, or define diverse arc segments, etc.

The distal end 120 of tip 100 has a chamfer 138 that defines an angle 139 relative to the longitudinal axis 110. The chamfer 138 ensures that burrs caused by machining are not present at the end of the dilator which may abrade soft cancellous bone. In one preferred form of the invention, the angle 139 of chamfer 138 is approximately 60 degrees.

The tip 100 has threads 140 which are configured so as to draw the dilator through bone and simultaneously compact the soft cancellous bone coming into contact with the threads 140. In one form of the invention, threads 140 advance the dilator through, and compact, the bone so as to create a bone tunnel in the bone. The threads 140 are preferably consistent along, and correspond to, the taper 105. In one preferred form of the invention, the threads 140 have a pitch 145 of about 0.060 to about 0.120 inches, and preferably about 0.080 inches. Inasmuch as the threads 140 are intended to dilate rather than cut bone, the threads are devoid of cutting flutes. As a result, the relatively blunt threads 140 displace, rather than cut, bone.

The body 200 is, preferably, cylindrical in shape, and preferably has a length 205 of about 0.406 inches. The distal end 210 of the body 200 has a threaded portion 215 comprising threads 220. The threads 140 of tip 100 continue, in a continuous fashion, as the threads 220 on the threaded portion 215 of body 200. In the case where the tip 100 defines a single, straight taper, the troughs of threads 220 continue to enlarge radially until they run out. However, the peaks of the threads 220 do not extend radially beyond, and are truncated along, an axial projection of the diameter 230 of the proximal unthreaded portion 231 of body 200. The peaks of the threads 220 of body 200 also may be truncated at a radial distance less than the axial projection of the proximal unthreaded portion 231, if desired.

In either case, the proximal unthreaded portion 231 defines the widest portion or tip perimeter of the dilator which is to enter the bone. Thus, the proximal unthreaded portion 231 is the last surface of the dilator that engates (and hence forms) the side wall of the bone tunnel. Accordingly, the quality of the surface of the proximal unthreaded portion 231 significantly influences the surface quality of the resultant bone tunnel. If a smooth bone tunnel surface is desired, the surface of the proximal unthreaded portion 231 should be completely smooth so as to not create a helical pattern of any sort in the bone tunnel wall while the dilator threadingtly advances into, or withdraws from the bone. The proximal unthreaded portion 231 also may include any number of projections or shape-forming structures thereon so as to impart desired pattern in the side wall of the bone tunnel which is being formed. To that end, body 200, tip 100 and threads 140 and 220 may be finished to a desired surface by polishing, coating or particularized machining.

The shaft 300 has a distal end 305 and a proximal end 310. The shaft 300 also may have indicia (not shown) such as depth marks or the like to aid in determining the dilator's penetration into a bone. The shaft 300 has a diameter 315 that may be the same as the diameter 230 of the proximal unthreaded portion 231 of body 200. Preferably, however, shaft 300 has a diameter or perimeter which is less than the diameter 230 or tip perimeter of the proximal unthreaded portion 231 of body 200. Where the diameter 315 is less than the diameter 230, the junction 320 should be machined so that, during removal of the dilator from a compacted bone tunnel, no sharp proximal edge exists that may be abrade the bone tunnel wall. Preferably, the junction defines an arced surface 325. However, any suitably-shaped surface which does not defeat the purposes of the invention may also be used.

The shaft 300 terminates in a proximal drive connector 400 which is adapted to connect with a manual or powered rotary driver (not shown). Preferably, the drive connector has a hexagonal-shaped or square-shaped cross-section. Alternatively, the drive connector may define a handle (not shown) for manual rotational driving.

Preferably, but not necessarily, tip 100, body 200 and shaft 300 are cannulated with a center bore 500. The cannulation is configured to receive a guidewire appropriate for dilation, as described below. In one preferred form of the invention, center bore 500 has a diameter of approximately 0.158 inches.

With the foregoing dilator, the preferred method of use does not involve pre-drilling or otherwise creating a sized hole in the bone.

In one preferred method of use, the surgeon drives a guidewire, such as a 2.4 mm K-wire, into the bone. Once the guidewire is positioned in the bone, the surgeon places the tip of cannulated dilator 5 over the guidewire. The surgeon then advances dilator 5 along the guidewire until the distal tip of the dilator engages the bone. Then the surgeon rotates dilator 5 clockwise so as to threadingly advance the dilator through the bone, until the dilator reaches a desired depth. Reaching the desired depth could be ascertained, for example, from indicia (not shown) on the shaft of the dilator. As dilator 5 follows the guidewire into the bone, the dilator drives interfering bone laterally, thereby opening a bone tunnel into the bone through dilation. After reaching the desired depth, the surgeon removes dilator 5 by rotating the dilator counterclockwise and retracting the dilator from the then-compacted bone tunnel.

This method creates a bone tunnel by dilation, without any substantial cutting or drilling of the bone. The method also can be practiced so as to cause significant compaction. For example, in the case where a 2.4 mm guidewire is used to define the path for the dilator, and a 10 mm dilator is used to dilate the bone along the path of the guidewire, the dilator provides a radial dilation (or compaction) of 3.8 mm about the circumference of the guidewire.

While dilator 5 can achieve substantial bone compaction, the dilator also compacts the bone gradually and gently because the peaks and troughs of its threads expand gradually. Specifically, as dilator 5 is rotated so as to advance the dilator through the bone, the bone is engaged by a thread peak that gradually expands. Thus, as the dilator advances through the bone, the portion of bone contacted by the thread peak will be gradually pushed outwardly as the thread peak progressively enlarges along the dilator's taper. As discussed above, radial thread peak expansion is limited within an axial projection of the proximal unthreaded portion 231 of body 200.

Just as bone contacted by the thread peak is gradually radially compacted, bone received in the thread trough is also gradually compacted an equivalent amount. As the dilator advances through the bone, the trough radially expands in a manner corresponding to taper 105. Thus, the portion of bone encountering the thread trough will also be gradually pushed outwardly. As described above, the dilator's threads begin at the distal end of tip 100 and run out on the distal portion of body 200. Just as the thread peak is limited by an axial projection of the unthreaded portion 231 of body 200, the thread trough also expands until it is co-extensive with the unthreaded portion 231. Naturally, if the thread peaks are truncated radially inward of the axial projection of the body, the thread trough also will be so limited.

As a result, bone contacted by the thread peaks, thread troughs, and the portions of the thread between the peaks and troughs, all are dilated and compacted in the same amount. The resultant bone tunnel exhibits even compaction along the length of the bone tunnel.

Although preferred, the dilator does not have to be cannulated. Instead, the dilator may be introduced into a small pilot hole formed in the bone. As the dilator threadingly and controllingly advances along the pilot hole, the dilator will accurately follow the path of the pilot hole in the bone and will not veer off course, as can be the case with prior art non-threaded dilators. This is due to the novel threaded taper of the present dilator 5, which induces the dilator to align itself as the dilator advances through the pilot hole.

Figure 4:
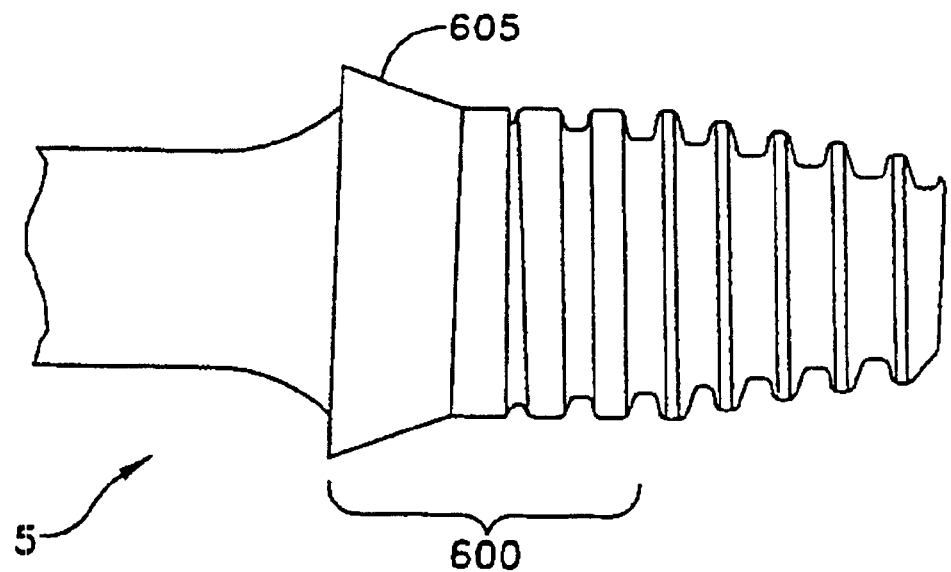
FIG. 4 is a side elevational view of another form of dilator formed in accordance with the present invention.
Figure 5:
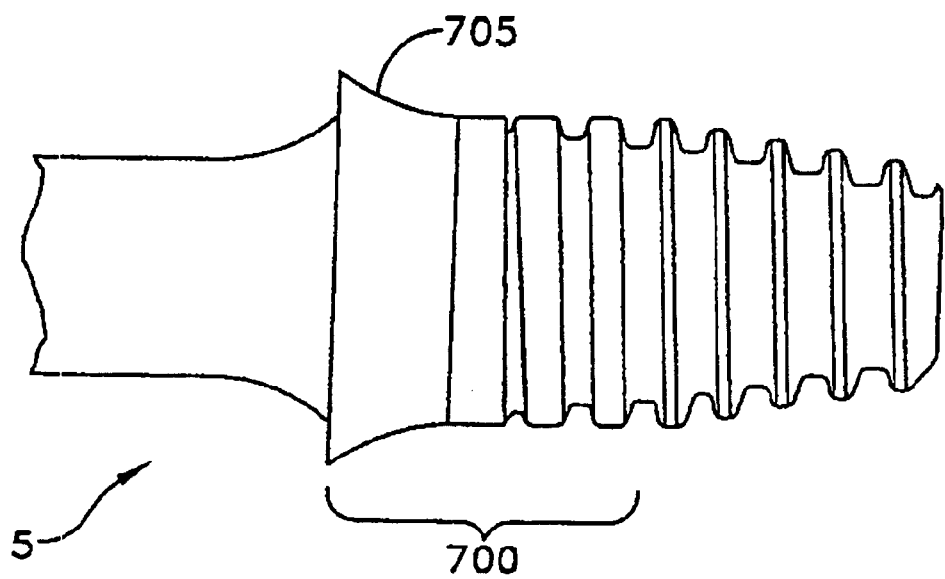
FIG. 5 is a side elevational view of yet another form of dilator formed in accordance with the present invention.

The present dilator may assume other configurations which render it more effective in dilating bone tunnels. For example, and referring now to FIG. 4, the body 600 may have a proximal linear taper 605, rather than the cylindrical shape of body 200. And referring next to FIG. 5, the body 700 may have a proximal arcuate flare 705. These configurations, and others not mentioned, may be employed to further displace the cancellous bone of the bone tunnel or contour the bone tunnel in a desirable manner.

Referring next to FIGS. 6–9, an additional embodiment 800 of the invention primarily dilates a bone tunnel, but also has a distal cutting flute 805 and/or a proximal cutting flute 810.

The distal cutting flute 805 aids in opening a passage through which the dilator 800 passes while forming a bone tunnel. More particularly, when the dilator 800 is dilating a bone tunnel, it threadingly advances through the bone tunnel, in a clockwise manner. As the dilator 800 rotates, the sharp edge 815 of the distal flute 805 cuts away soft cancellous bone encountered as the dilator 800 advances. Cutting away this inner-most bone matter of the passage facilitates passage of the dilator into the bone.

The proximal cutting flute 810 aids in removing the dilator 800 from a bone tunnel following dilation of the bone tunnel. More particularly, when the dilator 800 is removed from the bone tunnel, it threadingly withdraws from the bone tunnel, in a counterclockwise manner. As the dilator 800 threadingly withdraws, the sharp edge 820 of the proximal flute 810 cuts away any soft cancellous bone that may spring back into the bone tunnel following dilation, and/or any other bone matter that may encumber removal of the dilator from the bone tunnel. Cutting away this encroaching bone matter reduces resistance to removing the dilator 800 from the dilated bone tunnel.

It should be appreciated that distal cutting flute 805 is configured so that it will only cut bone while the dilator is advancing into the bone, and proximal cutting flute 810 is configured so that it will only cut bone while the dilator is withdrawing from bone.

To aid in determining whether the dilator is imparting an appropriate level of compaction and/or dilating in a sufficiently gentle manner, the dilator may include, or may be adaptable for connection to, a torque indicator to ascertain the amount of torque or stress that dilation is causing.

The invention is not limited to the foregoing, but also encompasses all improvements and substitutions consistent with the principles of the invention.

What is claimed is:

1. A dilator comprising:
   a tip having an axis and a thread disposed about said axis, said thread being defined by a peak and an adjacent trough, said trough having a radially expanding configuration toward a proximal end of said dilator until said trough is co-extensive with said peak;
   wherein said peak and said trough are adapted to substantially displace bone.

2. A dilator according to claim 1 wherein said tip defines a proximally-expanding taper.

3. A dilator according to claim 2 wherein said thread corresponds to said taper.

4. A dilator according to claim 2 wherein said taper is selected from the group consisting of straight, compound, parabolic, elliptical and diverse arc segment tapers.

5. A dilator according to claim 2 wherein said taper defines an angle of between about 5 and about 30 degrees with respect to said axis.

6. A dilator according to claim 2 wherein said taper defines an angle of about 10.85 degrees with respect to said axis.

7. A dilator according to claim 1 wherein said thread defines a pitch of between about 0.060 and about 0.120 inches.

8. A dilator according to claim 1 wherein said dilator further comprises a body having a surface with an axial projection, said body being mounted on said tip.

9. A dilator according to claim 8 wherein said body is cylindrical.

10. A dilator according to claim 1 wherein said trough proximally and radially expands until said trough is co-extensive with said peak.

11. A dilator according to claim 1 wherein said tip has a central opening configured to receive a guidewire.

12. A dilator according to claim 1 wherein said dilator further comprises a shaft, defining a shaft perimeter, mounted on said tip;
   wherein said tip defines a tip perimeter; and
   wherein said shaft perimeter is radially inferior to said tip perimeter.

13. A dilator according to claim 1 wherein said dilator is configured so that said peak and trough displace bone more than 2 mm.

14. A method for dilating bone comprising:
   threadingly advancing through a bone a dilator having a thread with a peak and a trough;
   wherein said peak and said trough are adapted to substantially displace bone; and
   wherein said trough has a radially expanding configuration toward a proximal-end of said dilator until said trough is co-extensive with said peak.

15. A method according to claim 14 wherein said trough displaces bone a substantially similar amount as said peak.

16. A method according to claim 14 wherein said method further comprises:
   driving a guidewire through a bone prior to said advancing; and
   placing said dilator on said guidewire prior to said advancing;
   wherein said advancing occurs along said guidewire.

17. A method according to claim 14 wherein said dilator includes a tip, said thread being disposed on said tip, and wherein said tip defines a proximally-expanding taper.

18. A method according to claim 17 wherein said thread corresponds to said taper.

19. A method according to claim 17 wherein said taper is selected from the group consisting of straight, compound, parabolic, elliptical and diverse arc segment tapers.

20. A method according to claim 17 wherein said taper defines an angle of between about 5 and about 30 degrees with respect to the longitudinal axis of said tip.

21. A method according to claim 17 wherein said taper defines an angle of about 10.85 degrees with respect to the longitudinal axis of said tip.

22. A method according to claim 17 wherein said dilator includes a body having a surface with an axial projection, said body being mounted on said tip.

23. A method according to claim 22 wherein said body is cylindrical.

24. A method according to claim 22 wherein said thread continues proximally about said body, the peak being truncated at or within the axial projection.

25. A method according to claim 17 wherein said tip defines a proximally-expanding taper with a tapered projection; and
   said thread corresponds to said tapered projection.

26. A method according to claim 17 wherein said tip has a central opening configured to receive a guidewire.

27. A method according to claim 14 wherein said thread defines a pitch of between about 0.060 and 0.120 inches.

28. A method according to claim 14 wherein said trough proximally and radially expands until said trough is co-extensive with said peak.

29. A dilator comprising:
   a tip having an axis and a thread disposed about said axis, said thread being defined by a peak and an adjacent trough, said trough having a radially expanding configuration toward a proximal end of said dilator until said trough is co-extensive with said peak;
   wherein said peak and said trough are adapted to substantially displace bone;
   wherein said trough proximally and radially expands until said trough is co-extensive with said peak.

30. A dilator comprising:
   a tip having an axis and a thread disposed about said axis, said thread being defined be a peak and an adjacent trough, said trough having a radially expanding configuration toward a proximal end of said dilator until said trough is co-extensive with said peak; and
   a body having a surface with an axial projection, said body being mounted on said tip;
   wherein said peak and said trough are adapted to substantially displace bone; and wherein said thread continues proximally about said body, said peak being truncated at or within said axial projection.

31. A dilator comprising:

a tip having an axis and a thread disposed about said axis, said thread being defined by a peak and an adjacent trough, said trough having a radially expanding configuration toward a proximal end of said dilator until said trough is co-extensive with said peak; and a shaft, defining a shaft perimeter, mounted on said tip;

wherein said peak and said trough are adapted to substantially displace bone;

wherein said tip defines a tip perimeter; and wherein said shaft perimeter is radially inferior to said tip perimeter.

32. A method for dilating bone comprising:

driving a guidewire into the bone;

placing a dilator, having a thread with a peak and a trough, on said guidewire; and threadingly advancing said dilator through said bone;

wherein said advancing occurs along said guidewire; and wherein said peak and said trough are adapted to substantially displace bone.

33. A method for dilating bone comprising:

creating a pilot hole in the bone; and threadingly advancing through said pilot hole a dilator having a thread with a peak and a trough;

wherein said peak and said trough are adapted to substantially displace bone.

34. A dilator comprising:

a tip having an axis and a thread disposed about said axis, said thread having a proximal end and a distal end, said trough having a radially expanding configuration toward a proximal end of said dilator until said trough is co-extensive with said peak;

wherein said thread is further defined by a smaller outside diameter at its distal end and a larger outside diameter at its proximal end; and wherein said thread is adapted over its entire length to gradually displace bone and form a bone tunnel.

35. A dilator comprising:

a tip having an axis and a thread disposed about said axis, said thread being defined by a peak and an adjacent trough, said trough having a radially expanding configuration toward a proximal end of said dilator until said trough is co-extensive with said peak;

wherein said peak and said trough are adapted to gradually displace bone, said trough displacing bone a substantially similar-amount as said peak, so as to relatively gently form a bone tunnel.

36. A dilator comprising:

a tip having a proximal end, a distal end and an axis extending between said proximal end and said distal end, and a thread disposed about said axis, said thread being defined by a peak and an adjacent trough, said trough having a radially expanding configuration toward a proximal end of said dilator until said trough is co-extensive with said peak;

wherein said peak and said trough are adapted to substantially displace bone;

and further wherein said thread extends to said distal end of said tip.

37. A dilator comprising:

a tip having an axis and a thread disposed about said axis, said thread being defined by a peak and an adjacent trough, said trough having a radially expanding configuration toward a proximal end of said dilator until said trough is co-extensive with said peak;

wherein said peak and said trough are adapted to substantially displace bone;

wherein said tip defines a proximally-expanding taper with a tapered projection, said thread corresponds to said tapered projection, and the taper at said trough extends along the entire length of said thread.

38. A method for dilating bone comprising:

threadingly advancing through a bone a dilator having a thread with a peak and a trough;

wherein said peak and said trough are adapted to substantially displace bone;

wherein said dilator includes a tip, said thread being disposed on said tip;

wherein said tip defines a proximally-expanding taper; and wherein said tip has a central opening configured to receive a guidewire.

* * * * *